United States Patent
Babler

(10) Patent No.: US 6,278,016 B1
(45) Date of Patent: Aug. 21, 2001

(54) METHODS FOR CONVERSION OF ISOPRENE TO PRENYL ALCOHOL AND RELATED COMPOUNDS

(75) Inventor: James H. Babler, Chicago, IL (US)

(73) Assignee: Loyola University of Chicago, Chicago, IL (US)

( * ) Notice: Subject to any disclaimer, the term of this patent is extended or adjusted under 35 U.S.C. 154(b) by 0 days.

(21) Appl. No.: 09/458,153

(22) Filed: Dec. 9, 1999

(51) Int. Cl.$^7$ ................................................ C07C 67/02
(52) U.S. Cl. ........................ 560/261; 560/129; 568/877
(58) Field of Search ...................... 560/261, 129; 568/877

(56) References Cited

U.S. PATENT DOCUMENTS

| | | | |
|---|---|---|---|
| 4,016,212 | 4/1977 | Leimgruber et al. | 260/614 |
| 4,567,265 | 1/1986 | Babler | 546/16 |
| 5,231,232 | 7/1993 | Babler | 568/393 |
| 5,349,071 | 9/1994 | Babler | 549/423 |
| 5,410,094 | 4/1995 | Babler | 568/662 |
| 5,471,005 | 11/1995 | Babler | 568/459 |
| 5,872,277 | 2/1999 | Babler | 560/261 |

FOREIGN PATENT DOCUMENTS

| | | |
|---|---|---|
| 2411530 | 9/1974 | (DE) . |
| 2423409 | 11/1974 | (DE) . |
| 2625074 | 12/1977 | (DE) . |
| 3021414 | 12/1980 | (DE) . |
| 21074 | 1/1981 | (EP) . |
| 344043 | 11/1989 | (EP) . |
| 77 14107 | 8/1972 | (JP) . |
| 52-10207 | 1/1977 | (JP) . |
| 60-239443 | 12/1985 | (JP) . |
| 61-22038 | 1/1986 | (JP) . |
| WO 91/09830 | 7/1991 | (WO) . |

OTHER PUBLICATIONS

Itoh et al., *Tetrahedron Lett.* 37, 91–92 (1996).
Kaneda et al., *J. Org. Chem.* 61, 4502–03 (1996).
Matsumato et al., *J. Org. Chem.* 49, 3435–36 (1984).
Julia et al., *Bull. Soc. Chim. France,* Part II, 588–600 (1980).
"The Merck Index," Ninth Edition, p. 956 (1976).
Takao et al., *Bull. Inst. Chem. Res.,* Kyoto Univ., 50 (4), 363–7 (1972).
"Organic Chemistry," Third Edition, Morrison & Boyd, p. 600.
Johnson et al., *Org. Synthesis,* 30, 18–21 (1950).

*Primary Examiner*—Paul J. Killos
*Assistant Examiner*—Robert W. Deemie
(74) *Attorney, Agent, or Firm*—Marshall, O'Toole, Gerstein, Murray & Borun

(57) ABSTRACT

Methods for preparing ester derivatives of 3-methyl-2-buten-1-ol (prenyl alcohol) from 2-methyl-1,3-butadiene (isoprene) and alkanoic acids in the presence of an inorganic acid catalyst are disclosed. The resultant prenyl ester (e.g., prenyl acetate) can be converted to prenyl alcohol by reaction with water in the presence of either a suitable enzyme or a base. Prenyl alcohol can be readily converted to citral, a chemical intermediate in the synthesis of vitamins A and E, and several widely-used carotenoids

18 Claims, No Drawings

METHODS FOR CONVERSION OF ISOPRENE TO PRENYL ALCOHOL AND RELATED COMPOUNDS

BACKGROUND OF THE INVENTION

1. Field of the Invention

The present invention relates to methods for preparing prenyl alcohol (3-methyl-2-buten-1-ol) (2) and ester derivatives of prenyl alcohol (2) from isoprene. Prenyl alcohol (2) is an intermediate in the manufacture of citral (5), a specialty chemical used in the flavor and fragrance industries, as well as in the manufacture of vitamins A and E, the anti-acne drugs tretinoin (sold by Ortho Pharmaceutical Corp. under the mark RETIN-A) and isotretinoin (sold by Hoffmann-La Roche Inc. under the name ACCUTANE), and several widely-used carotenoids, including beta-carotene.

2. Brief Description of Related Technology

One of the most expedient routes to citral (5) involves a thermal rearrangement of 3-methyl-1-(3-methyl-2-buten-1-oxy)-1,3-butadiene (4), which is readily obtained when acetal (3) [prepared from prenyl alcohol (2) and 3-methyl-2-butenal (prenal, (1))] is heated in the presence of a weak acid catalyst (e.g., acetic acid or 2,4-nitrophenol) at temperatures in the range of 125° C. to 150° C. The pathway by which unsaturated ether (4) is converted to citral (5) involves a Claisen rearrangement, followed by a subsequent Cope rearrangement in the same reaction vessel:

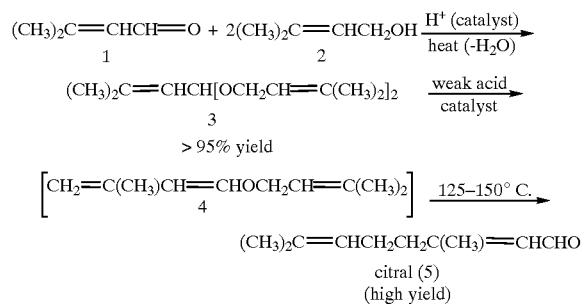

The approach to citral (5) described above has been known for more than 25 years and has continued to be developed to the stage where one is able to effect the conversion of prenal (1) and prenyl alcohol (2) to citral (5) in a "one-pot" process. See, European patent application EP 344,043 (Nov. 29, 1989) filed by Rhône-Poulenc [*Chem. Abstracts* 1990, 112, 179516d] and PCT Int. Appl. WO 91 09,830 (Jul. 11, 1991) [*Chem. Abstracts* 1991, 115, 114815t]. Previous patents have verified that unsaturated ether (4), obtained directly from acetal (3), can be converted to citral (5) in high yield (90–100%), e.g.:

(a) German patent 2,411,530 (Sep. 26, 1974 to Hoffmann-LaRoche): *Chem. Abstracts* 1975, 82, 4434k.

(b) U.S. Pat. No. 4,016,212 (Apr. 5, 1977 to Hoffmann-LaRoche): *Chem. Abstracts* 1977, 87, 136042u.

(c) German patent 2,423,409 (Nov. 28, 1974 to Teijin Ltd. of Japan): *Chem. Abstracts* 1979, 91, 123406y.

(d) German patent 2,625,074 (Dec. 8, 1977 to BASF): *Chem. Abstracts* 1978,88, 89114c.

(e) European patent application 21,074 (Jan. 7, 1981, filed by BASF): *Chem. Abstracts* 1981, 95, 7513q.

(f) Japanese patent 61 22,038 issued to Kuraray Co., Ltd.: *Chem. Abstracts* 1986, 10, 134188n.

The principal difficulty with the above process is the high cost of prenyl alcohol (2)—which is almost as costly as citral (5). Once prenyl alcohol (2) is obtained, however, it can be oxidized conveniently with air in the presence of various metallic or metallic salt catalysts to yield the corresponding aldehyde [prenal (1)]. Refer to: M. Matsumoto et al.,*J. Org. Chem.* 1984, 49, 3435; Japanese patent 60 239,443 issued to Kuraray Co., Ltd. [*Chem. Abstracts* 1986, 104, 148312q]; and K. Kaneda etal., *J. Org. Chem.* 1996, 61, 4502.

Isoprene [2-methyl-1,3-butadiene, $CH_2=C(CH_3)CH=CH_2$] would seem to be a useful and potentially low-cost precursor to prenyl alcohol (2). Isoprene, which is used to make "synthetic natural rubber," can be obtained by "cracking" petroleum or—more conveniently—by a Prins reaction involving isobutylene and formaldehyde.

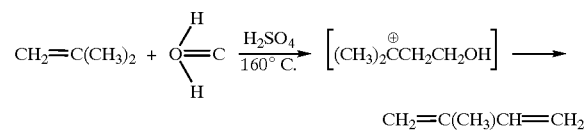

See, Japanese patent 71 14,107, issued to Sumitomo Chemical Co., Ltd. [*Chem. Abstracts* 1972, 77, 153520j].

Unfortunately, acid-catalyzed addition of water to isoprene yields only a minor amount of prenyl alcohol (2) and a substantial amount of the isomeric tertiary alcohol shown below.

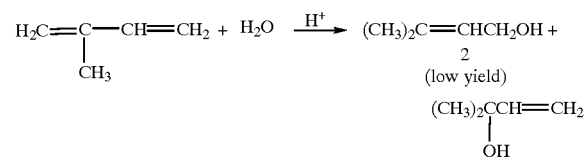

In addition to the above two alcohols, various other products are obtained in this reaction. See, *Chem. Abstracts* 1973, 78, 84547e.

Another approach to the formation of prenyl alcohol (2) from isoprene involves prenyl halide (6) $[(CH_3)_2C=CHCH_2X$, X=Br or Cl] intermediates. If one has prenyl halides (6) available, the following route to prenyl alcohol has been developed:

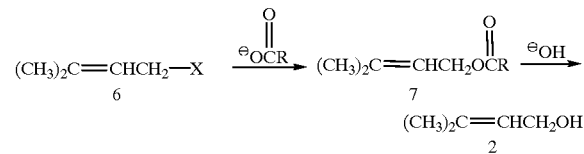

Refer to: Japanese patent 77 10,207 issued to Kuraray Co., Ltd. [*Chem. Abstracts* 1977, 87, 38852p] and German patent 3,021,414 (Dec. 11, 1980, issued to Montedison; *Chem. Abstracts* 1981, 94, 17431 1h).

Prenyl halides (6) can be formed by the addition of hydrohalic acids (FIX: HCl or HBr) to isoprene. Although this reaction does yield prenyl halides (6), yields are only moderate and the reaction is complicated by the fact that HX also adds to the double bond in the initially formed prenyl halide (6) to give a dihalide: $(CH_3)_2C(X)CH_2CH_2X$.

Furthermore, prenyl bromide (or chloride) is highly toxic, rather volatile, and decomposes if one attempts to distill it at atmospheric pressure.

Other methods for the conversion of isoprene to prenyl alcohol (2,) were reported by J. H. Babler in U.S. Pat. No. 5,872,277 (Feb. 16, 1999) (the '277 patent). In one particular method of the '277 patent, slow, preferably dropwise, addition of isoprene to a carboxylic acid (8) whose acid ionization constant, $K_a$, (relative to water) is greater than $10^{-4}$ yields the corresponding prenyl ester (7):

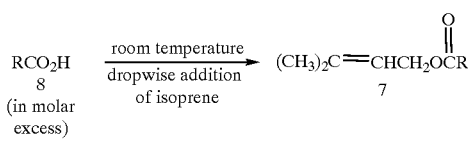

This reaction fails for acetic acid ($K_a=1.75\times10^{-5}$), propionic acid ($K_a=1.34\times10^{-5}$), et al., and is even quite slow when one uses formic acid ($K_a=1.77\times10^{-4}$). In contrast, the use of dichloroacetic acid ($K_a=5.53\times10^{-2}$) in molar excess in the above reaction results in a moderate yield of the corresponding prenyl ester (7), prenyl dichloroacetate. Once the ester (7) is obtained, it can be readily saponified using sodium carbonate, sodium hydroxide, potassium carbonate et al., in aqueous alcohol at room temperature to yield prenyl alcohol (2).

Although the addition of dichloroacetic acid to isoprene is useful for synthesis of small quantities of prenyl alcohol (2), the high cost of dichloroacetic acid requires that it be recovered after the saponification of prenyl dichloroacetate and subsequently recycled—a process that proved to be difficult to accomplish on a large scale.

SUMMARY OF THE INVENTION

Methods for converting isoprene to certain prenyl esters (7) in good yield have been developed.

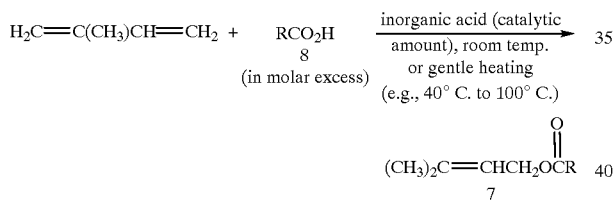

A preferred process involves addition of isoprene (bp: 34° C.) to a mixture including an alkanoic acid (8), $RCO_2H$, wherein R is a $C_1$–$C_4$ alkyl group, and an inorganic acid catalyst.

In another method of the invention, an inorganic acid catalyst is added to a mixture including an alkanoic acid (8), $RCO_2H$, wherein R is a $C_1$–$C_4$ alkyl group, and isoprene. Because the prenyl esters (7) will be subsequently hydrolyzed to prenyl alcohol (2) and the corresponding alkanoic acid (8), $RCO_2H$, mixtures of carboxylic acids, $RCO_2H$, can also be employed.

The above reaction will not occur unless the inorganic acid catalyst has a $K_a$ (relative to water) that is about $10^{-3}$ to about $10^{-6}$, preferably about $10^{-3}$ to about $10^{-2}$. Phosphoric acid [$K_a=7.1\times10^{-3}$; see: "The Merck Index," Ninth Edition, page 956] is a preferred catalyst for effecting the desired transformation [i.e., isoprene→prenyl ester (7)].

In contrast, organic acids such as dichloroacetic acid ($K_a=5.5\times10^{-2}$) or oxalic acid ($K_a=5.4\times10^{-2}$)[see: *Organic Chemistry*, Third Edition, page 600, by Morrison and Boyd] that are stronger than phosphoric acid failed to catalyze the process under reaction conditions for which phosphoric acid gave a high yield of prenyl ester (7)—e.g., no reaction occurred using dichloroacetic acid as the catalyst.

Although the addition of acetic acid to isoprene in the presence of a catalytic amount of phosphoric acid will occur slowly at room temperature to yield prenyl acetate (systematically named as 3-methyl-2-buten-1-yl acetate), gentle heating of the reaction mixture in a pressure vessel at temperatures of approximately 40° C. to 100° C. is preferred if one wishes to conduct the process in several hours.

Undiluted (100%) phosphoric acid is preferred, however, diluted solutions (e.g., 85% phosphoric acid, 15% water) also are useful in the invention. Optionally, if one uses a diluted phosphoric acid as the catalyst, then addition of a desiccant is preferred because, in the absence of water, the desired transformation [isoprene→prenyl ester (7)] proceeds more rapidly, and by-products, such as the tertiary alcohol, are not formed. Suitable desiccants for use in the invention include, but are not limited to, acetic anhydride, zeolites, and molecular sieves. Acetic anhydride is preferred because it reacts with the water present in a diluted acid to generate acetic acid.

If one adds a very strong acid having a $K_a$ (relative to water) that is greater than about $10^6$ [e.g., sulfuric acid $K_a=10^9$) or p-toluenesulfonic acid ($K_a=3.2\times10^{-6}$)] to the mixture of isoprene and a representative alkanoic acid (8) such as acetic acid, the desired reaction will occur; however, yields of prenyl esters (7) are low (less than 25%), due to sensitivity of the initial prenyl ester product (1) to strongly acidic conditions, which causes the initial prenyl ester product (7) to undergo subsequent transformations.

Once the prenyl ester (7) is obtained, it can be readily saponified using sodium carbonate, sodium hydroxide, potassium carbonate, et al., in aqueous alcohol. More conveniently, esters such as prenyl acetate can be easily hydrolyzed to prenyl alcohol (2) (and acetic acid) by use of lipase enzymes:

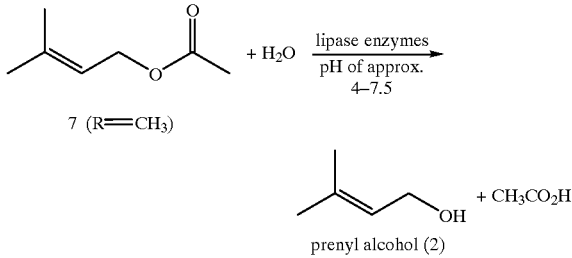

See, T. Itoh, et al., *Tetrahedron Let.* 1996, 37, 91.

No tertiary alcohol esters (9), isomeric with (7), were observed in the products formed in the process of the present invention wherein isoprene was added to a mixture including acetic acid and a phosphoric acid catalyst.

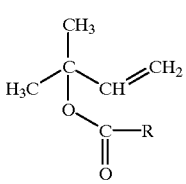

In contrast, when water is added to isoprene, a major product is the tertiary alcohol, $(CH_3)_2C(OH)CH=CH_2$. See, *Chem. Abstracts* 1973, 78, 84547e.

The process of the present invention is believed to involve protonation of isoprene to yield the prenyl cation intermediate $(CH_3)_2C\!=\!CHCH_2^+$ prior to formation of prenyl ester (7). This cation is known to react with unsaturated esters [such as $CH_2\!=\!C(CH_3)CH_2CH_2OC(\!=\!O)CH_3$] similar to the structure of prenyl ester (X). See, Table X entries 5 and 7 on page 595 of Julia and coworkers: *Bull. Soc. Chim. France*, 1980, Part II, 588. Entry 5 refers to the following reaction:

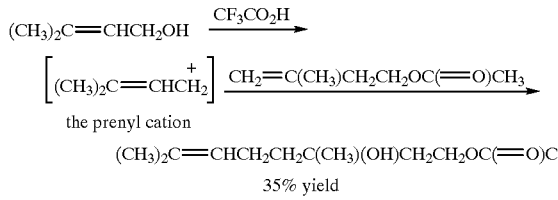

35% yield

Entry 7 of the Julia article is similar; however, it uses formic acid in molar excess and a prenyl ester (7) (i.e., prenyl formate) to generate the prenyl cation.

Thus, the literature teaches that the prenyl cation (generated in the presence of carboxylic acids) adds readily to the alkene functionality in unsaturated esters to give higher molecular weight adducts—terpenes in the examples cited above. Since the process of the present invention involves both the prenyl cation (generated by protonation of isoprene) and unsaturated esters [i.e., formation of prenyl esters (7)], the obtention of the latter (7) in high yield was surprising. Based on the prior art, one would expect subsequent reaction of the initially-formed unsaturated prenyl ester (2), in the presence of a carboxylic acid, to react with the prenyl cation—eventually leading to dimeric products.

Preferred Process Steps

The following are preferred elements in the processes of the present invention:

(a) an alkanoic acid, $RCO_2H$ wherein R is a $C_1$–$C_4$ alkyl group, preferably acetic acid, in molar excess; mixtures of such acids can also be used;

(b) an inorganic acid catalyst, having a $K_a$ (relative to water) that is about $10^{-3}$ to about $10^6$, preferably about $10^{-3}$ to about $10^2$. Phosphoric acid and polyphosphoric acid are especially preferred catalysts for this process; and (c) isoprene (systematically named as 2-methyl-1,3-butadiene).

The following reaction conditions can be used. The reaction occurs at room temperature, thus heating is not essential. However, absent heating, the reaction is slow. Hence, gentle heating (about 40° C. to about 100° C.) of the reaction mixture under pressure (due to the volatility of isoprene) is preferred.

A preferred reaction for forming citral (5) from isoprene using acetic acid in molar excess and phosphoric acid as the catalyst is as follows. In step A, prenyl acetate is formed.

Step A:

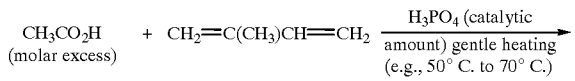

-continued $(CH_3)_2C\!=\!CHCH_2OC(\!=\!O)CH_3$ prenyl acetate
(3-methyl-2-butenyl acetate)
(insoluble in water; miscible with heptane, octane, et al.)

Product isolation is rather easy: either continuously extract the prenyl acetate product from the mixture using a non-polar organic solvent such as heptane, or partition the mixture between the non-polar solvent and water. The excess acetic acid and phosphoric acid remain in the aqueous phase, from which they easily can be recovered. In Step B of the preferred process, prenyl acetate is saponified using sodium hydroxide or sodium carbonate in aqueous methanol to yield prenyl alcohol (2).

Step B:

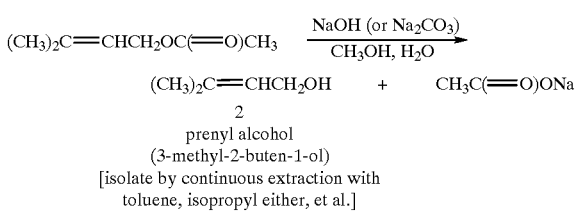

2
prenyl alcohol
(3-methyl-2-buten-1-ol)
[isolate by continuous extraction with toluene, isopropyl either, et al.]

One can also hydrolyze prenyl acetate to prenyl alcohol (2) in the presence of a lipase enzyme as described by T. Itoh et al., *Tetraedron Lett*. 1996, 37, 91.

Once prenyl alcohol (2) is obtained it can be oxidized conveniently with air in the presence of various metallic or metallic salt catalysts to yield the corresponding aldehyde [prenal (1)], in Step C.

Step C:

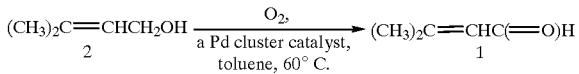

See, K. Kaneda et al., *J. Org. Chem*. 1996, 61, 4502.

At least two routes can be used to form citral from prenyl alcohol (2) and prenal (1). In the first route, step $D_1$, acetal (3) is first prepared from prenyl alcohol (2) and prenal (1) by reaction of prenal (1) with two molar equivalents of prenyl alcohol (2) in the presence of an acid catalyst with simultaneous removal of water from the reaction mixture.

Step $D_1$:

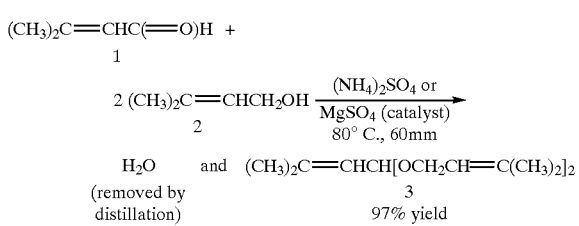

Reference: *Chem. Abstracts* 1986, 105, 134188n.

Then, acetal (3) is heated in the presence of a weak acid catalyst, e.g. adipic acid, at 150° C. to yield 3-methyl-1-(3-methyl-2-buten-1-oxy)-1,3-butadiene (4) and prenyl alcohol (2). A subsequent Claisen rearrangement, followed by a Cope rearrangement, yields citral (5).

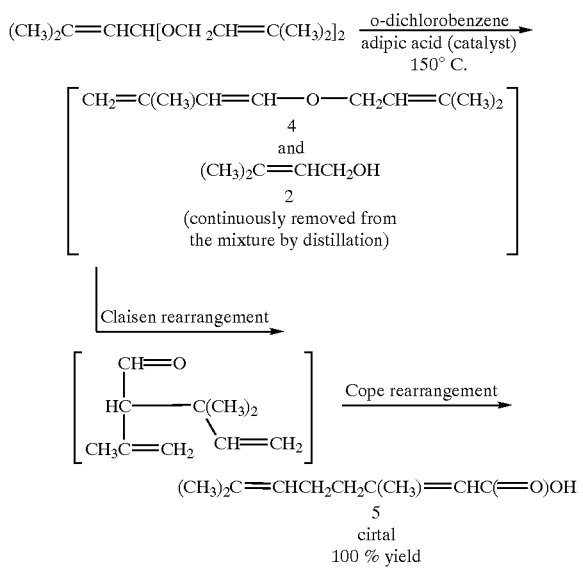

Alternatively, citral (5) can be formed from prenyl alcohol (2) and prenal (1) in a "one-pot" process, step D₂.

Step D₂:

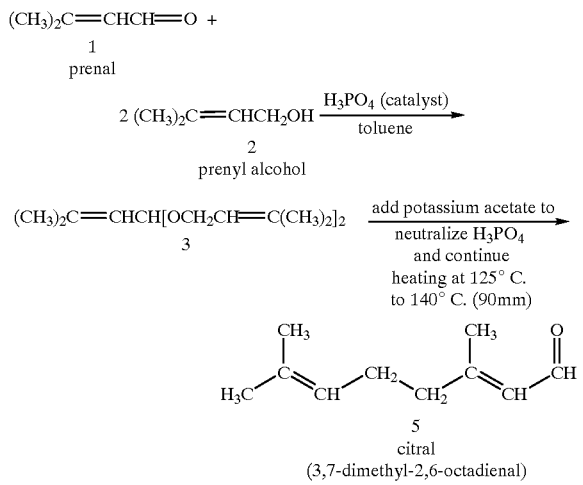

Reference: *Chem. Abstracts* 1991, 115, 114815t.

DETAILED DESCRIPTION OF THE PREFERRED EMBODIMENTS

The following examples are presented for purposes of illustration and should not be construed as limiting the invention which is delineated in the claims.

EXAMPLES

The following examples are provided to illustrate the invention but are not intended to limit the scope of the invention.

Example I

Preparation of 3-Methyl-2-buten-1-yl Acetate by Treatment of Isoprene With Acetic Acid Containing Phosphoric Acid and Acetic Anhydride To a solution of 1.00 mL (10.6 mmoles) of acetic anhydride in 10 mL of glacial acetic acid was added 0.50 mL (7.3 mmoles) of 85% phosphoric acid. This mixture, while being continuously protected from exposure to atmospheric moisture, was stirred at room temperature for 15 minutes to destroy water present in the aqueous phosphoric acid. The mixture was then transferred via pipette to a 15 mL pressure vessel (heavy glass wall, purchased from Chemglass, Vineland, N.J.). After adding a small spin bar and 0.5 mL (5.0 mmoles) of isoprene (purchased from Aldrich Chemical Co., Milwaukee, Wis.), the vessel was closed and the mixture was heated, with continuous stirring, at 62° C. (external oil bath temperature) for 3 hours. After cooling the mixture to room temperature, the product was isolated by dilution of the reaction mixture with 120 mL of water and extraction with hexane. After subsequent washing of the organic layer with water (1×100 mL), saturated aqueous sodium bicarbonate (1×50 mL), and saturated aqueous sodium chloride (1×50mL), it was dried over anhydrous magnesium sulfate and filtered. Removal of most of the hexane by fractional distillation at atmospheric pressure, followed by removal of residual hexane at reduced pressure (60 mm Hg), and subsequent evaporative distillation, yielded 325 mg (51% yield) of the named ester: boiling point 70° C. to 75° C. (bath temperature, 6.5 mm Hg). The weight of the residue in this distillation was 30 mg, which presumably consisted of a mixture of higher-molecular-weight products obtained when the "prenyl cation" (formed by addition of a proton to isoprene) reacted with a molecule of isoprene in lieu of acetic acid. To verify this hypothesis, two additional experiments were conducted during which only the amount of isoprene was changed. As expected, use of 0.25 mL (2.5 mmoles) of isoprene yielded a product containing only trace (<5%) amounts of high-boiling by-products; whereas use of 1.00 mL (10.0 mmoles) of isoprene resulted in an increase in the formation of such by-products. To maximize the conversion of isoprene to prenyl acetate, gradual addition of isoprene to the heated reaction mixture over a period of 1–2 hours, followed by heating for an additional 2 hours at 60° C. to 65° C., is recommended.

The identity and purity of this compound was ascertained by IR and proton NMR analysis (recorded at 300 MHz). The latter spectrum exhibited a broad triplet (J=7.2 Hz) at δ 5.35 (CH=C), a doublet (J=7.2 Hz) at δ 4.57 (CH₂O), a singlet at δ 2.05 (CH₃C=O), and signals for two vinyl methyl groups at δ 1.76 and 1.71.

The low material balance in this experiment can be explained by the volatility of isoprene (bp 34° C.) and use of inadequate pressure equipment. Indeed, continued heating of the reaction mixture (5 hours or more) did not result in the isolation of a larger amount of crude product and should be avoided since the product very slowly undergoes further transformations upon prolonged heating of the reaction mixture.

Example II

Preparation of 3-Methyl-2-buten-1-yl Acetate by Treatment of Isoprene With Acetic Acid Containing Aqueous Phosphoric Acid as a Catalyst Glacial acetic acid (10 mL), isoprene (0.25 mL, 2.5 mmoles), and 85% phosphoric acid (0.50 mL) were added to a 15 mL pressure vessel (heavy glass wall, purchased from Chemglass, Vineland, N.J.). After adding a small spin bar, the vessel was closed and the mixture was heated, with continuous stirring, at 60° C. to 62° C. (external oil bath temperature) for 4 hours. After cooling the mixture to room temperature, the product was isolated as described in the procedure of Example I, yielding 64 mg (20% yield) of the named ester. Although the desired transformation occurred, the process proceeds more slowly in the presence of water (approximately 7 mmoles in 0.50 mL of 85% phosphoric acid).

Example III

Preparation of 3-Methyl-2-buten-1-yl Propionate by Treatment of Isoprene With Propionic Acid Containing Aqueous Phosphoric Acid as a Catalyst Propionic acid (10 mL), isoprene (0.50 mL, 5.0 mmoles), and 85% phosphoric acid (0.50 mL) were added to a 15 mL pressure vessel (heavy glass wall). After adding a small spin bar, the vessel was closed and the mixture was heated, with continuous stirring, at 60° C. (external oil bath temperature) for 3 hours. After cooling the mixture to room temperature, the product was isolated by dilution of the reaction mixture with 100 mL of water and extraction with hexane. After subsequent washing of the organic layer with water (2×100 mL), 10% (w/v) aqueous sodium hydroxide (100 mL), and saturated aqueous sodium chloride (1×50 mL), it was dried over anhydrous magnesium sulfate and filtered. Removal of the hexane by evaporation at reduced pressure yielded 55 mg (8% yield) of the named ester. The identity of this compound was ascertained by IR and proton NMR analysis (recorded at 300 MHz). The latter spectrum exhibited a broad triplet (J=7.2 Hz) at $\delta$ 5.35 (CH=C), a doublet (J=7.2 Hz) at $\delta$4.58 (CH$_2$O), a quartet (J=7.5 Hz) at $\delta$ 2.33 (CH$_2$C=O), signals for two vinyl methyl groups at $\delta$ 1.76 and 1.71, and a triplet (J=7.5 Hz) at $\delta$ 1.14 (CH$_3$).

Example IV

Preparation of 3-Methyl-2-buten-1-yl Acetate by Treatment of Isoprene With Acetic Acid Containing Polyphosphoric Acid as a Catalyst To a 25 mL, 1-neck reaction flask fitted with a glass stopper was added a small spin bar, 150 mg of polyphosphoric acid, and 12 mL of glacial acetic acid. After stirring this mixture at room temperature for 15 minutes, it was transferred via pipette to a 15 mL pressure vessel (heavy glass wall). After adding a small spin bar and 0.50 mL (5.0 moles) of isoprene, the vessel was closed and the mixture was heated, with continuous stirring, at 45° C. (external oil bath temperature) for 2 hours. After cooling the mixture to room temperature, the product was isolated as described in the procedure of Example I, yielding 53 mg (8% yield) of the named ester. A similar experiment was conducted at room temperature; however, the reaction was quite slow, and prenyl acetate was obtained in a yield of only 5% after a reaction time of 10 hours.

Example V

Treatment of Isoprene with Acetic Acid Containing Dichloroacetic Acid as a Catalyst Dichloroacetic acid (0.50 mL, 6.1 mmoles; purified-grade, purchased from Fisher Scientific Co.), glacial acetic acid (10 mL), and isoprene (0.50 mL, 5.0 mmoles) were added to a 15 mL pressure vessel (heavy glass wall). After adding a small spin bar, the vessel was closed and the mixture was heated, with continuous stirring, at 60° C. to 62° C. (external oil bath temperature) for 3 hours. After cooling the mixture to room temperature, the product was isolated as described in the procedure of Example I, yielding only 12 mg of material, the proton NMR spectrum of which detected none of the named ester.

Example VI

Preparation of 3-Methyl-2-buten-1-yl Acetate by Treatment of Isoprene With Excess Acetic Acid in the Presence of a Strong Acid Catalyst ($K_a$>10$^6$)

1.00 mL (10.0 mmoles) of isoprene and a solution of 195 mg (1.03 mmoles) of p-toluenesulfonic acid monohydrate $K_a$ (relative to water)=3.2×10$^6$) in 15 mL of glacial acetic acid were added to a 25 mL, 1-neck reaction flask fitted with a glass stopper (to minimize loss of the volatile isoprene). This mixture was subsequently stirred at room temperature for 3 hours. Isolation of the product as described in the procedure of Example I afforded 218 mg [17% yield if this was solely the named ester (prenyl acetate)] of crude material, shown by proton NMR analysis to be a complex mixture of prenyl acetate (less than one-half of the mixture) and higher molecular-weight by-products. A subsequent experiment was conducted to verify that, when treated with acetic acid in the presence of a strong acid catalyst such as p-toluenesulfonic acid, prenyl acetate undergoes further transformations—even at room temperature.

Example VII

Preparation of 3-Methyl-2-buten-1-ol (Prenyl Alcohol) by Saponification of Prenyl Acetate.

260 mg (2.03 moles) of 3-methyl-2-buten-1-yl acetate, produced from isoprene in accordance with Example I, 3.0 mL of methyl alcohol, and 0.60 mL of 5M aqueous sodium hydroxide (3.0 mmoles) were added to a reaction flask equipped with an efficient reflux condenser connected to an apparatus similar to that described by Johnson and Schneider [*Org. Synth.*, 30, 18 (1950)] so that the mixture in the flask could be protected from atmospheric conditions throughout the course of the reaction. This mixture was subsequently heated at 60° C. to about 65° C. (external oil bath temperature) for 2 hours. After cooling the mixture to room temperature, the product was isolated by dilution of the reaction mixture with 30 mL of saturated aqueous sodium chloride and extraction with 20 mL of 1:1 (v/v) pentane:ether. After subsequent washing of the organic layer with saturated aqueous sodium chloride (25 mL), it was dried over anhydrous magnesium sulfate and filtered. Removal of most of the volatile organic solvents by fractional distillation at atmospheric pressure, followed by removal of residual pentane at reduced pressure (50 to 60 mm), afforded 149 mg (85% yield) of the named alcohol, the IR and proton NMR spectral properties of which were identical to those exhibited by an authentic sample of 3-methyl-2-buten-1-ol (purchased from Aldrich Chemical Co., Milwaukee, Wis.).

On a large scale, it may be more convenient to hydrolyze prenyl acetate in the presence of a lipase enzyme. See, T. Itoh et al., *Tetrahedron Lett.*, 37, 91 (1996).

What is claimed is:

1. A method of preparing prenyl esters of the formula (CH$_3$)$_2$C=CHCH$_2$OC(=O)R, wherein R is a C$_1$–C$_4$ alkyl group, comprising the steps:
    (a) forming a reaction mixture comprising a carboxylic acid of the formula RCO$_2$H, wherein R is a C$_1$–C$_4$ alkyl group, and an inorganic acid catalyst; and
    (b) adding isoprene to the reaction mixture, while maintaining said carboxylic acid in molar excess;

wherein the inorganic acid catalyst has a $K_a$ (relative to water) of about $10^{-3}$ to about $10^6$.

2. The method of claim 1 wherein said inorganic acid catalyst has a $K_a$ (relative to water) of about $10^{-3}$ to about $10^2$.

3. The method of claim 1 wherein said reaction mixture further comprises a desiccant.

4. The method of claim 3 wherein said desiccant comprises an anhydride selected from the group consisting of acetic anhydride and propionic anhydride.

5. The method of claim 1 wherein said carboxylic acid comprises acetic acid.

6. The method of claim 1 wherein said reaction mixture of step (a) comprises a mixture of carboxylic acids of the formula $RCO_2H$, wherein R is a $C_1$–$C_4$ alkyl group, and an inorganic acid catalyst.

7. The method of claim 1 wherein said acid catalyst comprises phosphoric acid.

8. The method of claim 7 wherein said acid catalyst comprises about 85% to about 100% phosphoric acid.

9. The method of claim 1 wherein said acid catalyst comprises polyphosphoric acid.

10. The method of claim 1 wherein said reaction mixture is maintained in a pressure vessel at a temperature of about 40° C. to about 100° C.

11. The method of claim 1 wherein step (b) is performed in dropwise fashion, over a period of several hours.

12. The method of claim 10 wherein isoprene is added slowly to said reaction mixture.

13. A method of preparing prenyl esters comprising the steps:

(a) forming a reacting mixture comprising a carboxylic acid of the formula $RCO_2H$, wherein R is a $C_1$–$C_4$ alkyl group, and isoprene; and (b) adding an inorganic acid catalyst to the reaction mixture; wherein the inorganic acid catalyst has a $K_a$ (relative to water) of about $10^{-3}$ to about $10^6$ and said carboxylic acid is maintained in molar excess of said isoprene.

14. The method of claim 13 wherein said inorganic acid catalyst has a $K_a$ (relative to water) of about $10^{-3}$ to about $10^2$.

15. The method of claim 13 wherein said carboxylic acid comprises acetic acid.

16. The method of claim 13 wherein said inorganic acid catalyst comprises phosphoric acid.

17. A method of preparing citral comprising the steps:

(a) forming a reaction mixture comprising a carboxylic acid of the formula $RCO_2H$, wherein R is a $C_1$–$C_4$ alkyl group, and an inorganic acid catalyst having a $K_a$ (relative to water) of about $10^{-3}$ to about $10^6$;

(b) adding isoprene to the reaction mixture, while maintaining said carboxylic acid in molar excess;

(c) isolating a prenyl ester from the reaction mixture;

(d) forming prenyl alcohol from the prenyl ester;

(e) oxidizing at least some of the prenyl alcohol to form prenal; and (f) forming citral from the prenyl alcohol and the prenal.

18. The method of claim 17 wherein said inorganic catalyst has a $K_a$ (relative to water) of about $10^{-3}$ to about $10^2$.

* * * * *

UNITED STATES PATENT AND TRADEMARK OFFICE
CERTIFICATE OF CORRECTION

PATENT NO. : 6,278,016 B1
DATED : August 21, 2001
INVENTOR(S) : James H. Babler

Page 1 of 1

It is certified that error appears in the above-identified patent and that said Letters Patent is hereby corrected as shown below:

<u>Title page,</u>
FOREIGN PATENT DOCUMENTS, delete "77 14107" and insert -- 71 14,107 --; and delete "52-10207" and insert -- 77 10,207 --.

Signed and Sealed this

Twenty-first Day of May, 2002

Attest:

Attesting Officer

JAMES E. ROGAN
*Director of the United States Patent and Trademark Office*